United States Patent
Delehanty et al.

(10) Patent No.: US 10,780,185 B2
(45) Date of Patent: Sep. 22, 2020

(54) MULTIFUNCTIONAL NANOPARTICLE BIOCONJUGATES FOR PHOTOACOUSTIC-BASED RECORDING OF CELLULAR MEMBRANE POTENTIAL

(71) Applicant: The Government of the United States of America, as represented by the Secretary of the Navy, Arlington, VA (US)

(72) Inventors: James B. Delehanty, Washington, DC (US); Michael H. Stewart, Springfield, VA (US); Okhil Nag, Alexandria, VA (US); Jeffrey R. Deschamps, Laurel, MD (US); Kimihiro Susumu, Alexandria, VA (US); Eunkeu Oh, Alexandria, VA (US); Lauren D. Field, College Park, MD (US); Alexander L. Efros, Annandale, VA (US); Alan L. Huston, Aldie, VA (US); Igor L. Medintz, Springfield, VA (US); Philip E. Dawson, San Diego, CA (US); Nashaat Rasheed, Fairfax, VA (US); Parag V. Chitnis, Fairfax, VA (US); John R. Cressman, Fairfax, VA (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 227 days.

(21) Appl. No.: 16/031,094

(22) Filed: Jul. 10, 2018

(65) Prior Publication Data
US 2018/0326097 A1    Nov. 15, 2018

Related U.S. Application Data

(63) Continuation-in-part of application No. 15/882,259, filed on Jan. 29, 2018.

(60) Provisional application No. 62/452,097, filed on Jan. 30, 2017.

(51) Int. Cl.
*A61K 49/22* (2006.01)
*G01N 33/58* (2006.01)
*G01N 33/542* (2006.01)

(52) U.S. Cl.
CPC .......... *A61K 49/222* (2013.01); *A61K 49/221* (2013.01); *G01N 33/542* (2013.01); *G01N 33/588* (2013.01)

(58) Field of Classification Search
CPC .. A61K 49/222; A61K 49/221; G01N 33/542; G01N 33/588

USPC ......................................................... 435/29
See application file for complete search history.

(56) References Cited

U.S. PATENT DOCUMENTS 6,662,040 B1    12/2003   Henrichs et al.

OTHER PUBLICATIONS

Nag et al., Quantum Dot-Peptide-Fullerene Bioconjugates for Visualization of in Vitro and in Vivo Cellular Membrane Potential, ACS NANO, vol. 11, (May 17, 2017), pp. 5598-5613.*
Zhang et al., Recording Membrane Potential Changes through Photoacoustic Voltage Sensitive Dye, Proc. of SPIE BiOS, vol. 10064, (Mar. 22, 2017), pp. 1-10.*
Algar et al., Quantum dots as platforms for charge transfer-based biosensing: challenges and opportunities, Journal of Materials Chemistry B, vol. 2, (2014), pp. 7816-7827.*
Boeneman et al., Selecting Improved Peptidyl Motifs for Cytosolic Delivery of Disparate Protein and Nanoparticle Materials, ACS Nano, vol. 7, No. 5, (2013), pp. 3778-3796.*
D. Wang, Y. Wu, and J. Xia, "Review on photoacoustic imaging of the brain using nanoprobes," Neurophotonics 3, 010901 (2016).
N. Dana, R. A. Fowler, A. Allen, J. Zoldan, L. Suggs, and S. Emelianov, "In vitro photoacoustic sensing of calcium dynamics with arsenazo III," Laser Physics Letters 13, 075603 (2016).
S. Chemla and F. Chavane, "Voltage-sensitive dye imaging: Technique review and models," Journal of Physiology—Paris 104, 40-50 (2010).
J. Yao and L. V. Wang, "Photoacoustic brain imaging: from microscopic to macroscopic scales," Neurophotonics 1, 011003-011003 (2014).
S. Hu and L. V. Wang, "Neurovascular Photoacoustic Tomography," Frontiers in Neuroenergetics 2(2010).
N. Vogt, "Voltage sensors: challenging, but with potential," Nature Methods 12, 921-924 (2015).

* cited by examiner

*Primary Examiner* — Jennifer M. H. Tichy
(74) *Attorney, Agent, or Firm* — US Naval Research Laboratory; Roy Roberts

(57) ABSTRACT

A construct for detecting cellular membrane potential includes a nanoparticle operable as an electron donor; a modular peptide attached to the nanoparticle, the peptide comprising a nanoparticle association domain, a motif configured to mediate peptide insertion into the plasma membrane, and at least one attachment point for an electron acceptor positioned at a controlled distance from the nanoparticle; and an electron acceptor. The nanoparticle can be a quantum dot and the electron acceptor can be $C_{60}$ fullerene. Photoacoustic emission from the construct correlates with cellular membrane potential.

3 Claims, 9 Drawing Sheets
Specification includes a Sequence Listing.

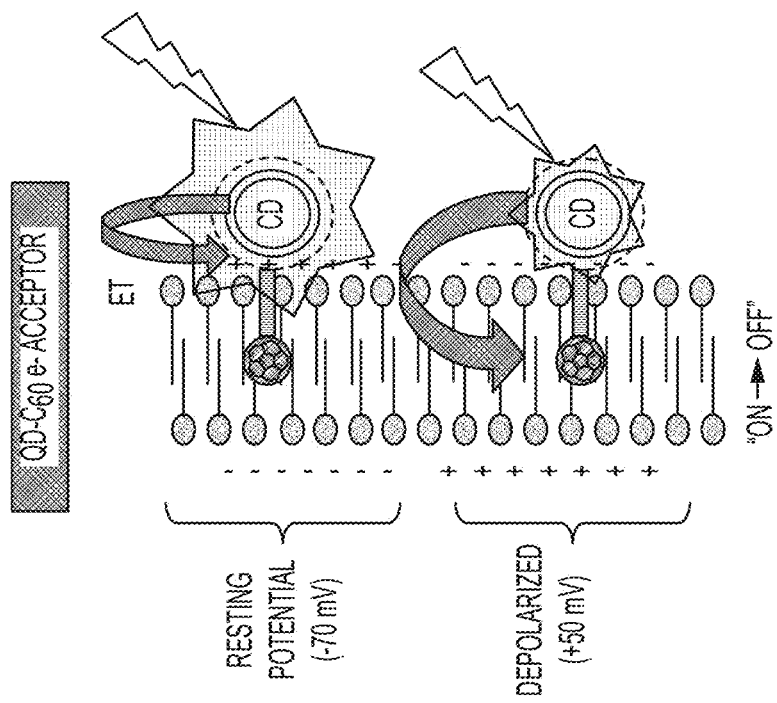
FIG. 1C
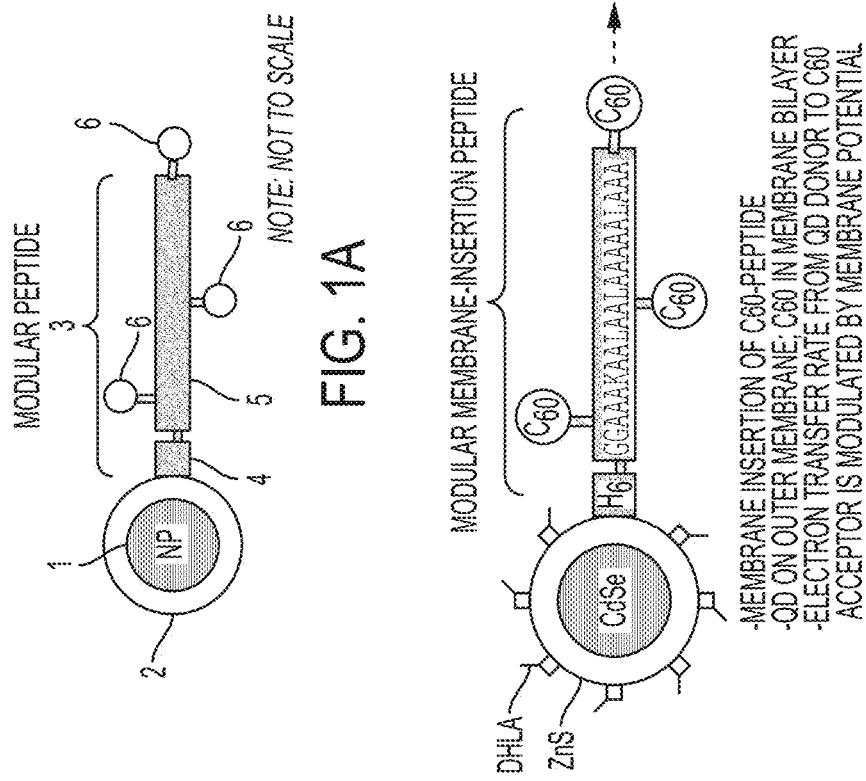
FIG. 1A
FIG. 1B

SEQUENCE LISTING

<160> NUMBER OF SEQ ID NOS: 3

<210> SEQ ID NO 1
<211> LENGTH: 28
<212> TYPE: PRT
<213> ORGANISM: Artificial Sequence
<220> FEATURE:
<223> OTHER INFORMATION: synthetic construct

<400> SEQUENCE: 1

Ala Ala Ala Ala Leu Ala Ala Ala Ala Leu Ala Ala Leu Ala Ala
1               5                   10                  15

Lys Ala Ala Ala Gly Gly His His His His His His
            20                  25

<210> SEQ ID NO 2
<211> LENGTH: 28
<212> TYPE: PRT
<213> ORGANISM: Artificial Sequence
<220> FEATURE:
<223> OTHER INFORMATION: synthetic construct

<400> SEQUENCE: 2

Lys Ala Ala Ala Leu Ala Ala Ala Ala Leu Ala Ala Trp Ala Ala
1               5                   10                  15

Leu Ala Ala Ala Gly Gly His His His His His His
            20                  25

<210> SEQ ID NO 3
<211> LENGTH: 37
<212> TYPE: PRT
<213> ORGANISM: Artificial Sequence
<220> FEATURE:
<223> OTHER INFORMATION: synthetic construct

<400> SEQUENCE: 3

Lys Ala Ala Ala Leu Ala Ala Ala Ala Leu Ala Ala Trp Ala Ala
1               5                   10                  15

Leu Ala Ala Ala Pro Pro Pro Pro Pro Pro Pro Pro Gly Gly His
            20                  25                  30

His His His His His
        35

MULTIFUNCTIONAL NANOPARTICLE BIOCONJUGATES FOR PHOTOACOUSTIC-BASED RECORDING OF CELLULAR MEMBRANE POTENTIAL

CROSS-REFERENCE TO RELATED APPLICATIONS

This Application claims the benefit of U.S. Provisional Patent Application No. 62/452,097 and is a Continuation-In-Part of U.S. patent application Ser. No. 15/882,259 filed on Jan. 29, 2018, the entirety of each of which is incorporated herein by reference.

BACKGROUND

A need exists for techniques to ascertain cellular membrane potential.

BRIEF SUMMARY

A modular, multifunctional nanoparticle (NP)-based electron donor-acceptor bioconjugate allows for the realtime perception of changes in cellular membrane potential. The construct includes the following components: (a) a photoluminescent NP electron donor; (b) a modular, multidomain membrane insertion peptide; and (c) an electron acceptor. The peptide includes (1) a NP association domain, (2) amino acid motifs to mediate peptide insertion into the plasma membrane, (3) one or more attachment points for attachment of an electron acceptor at discreetly controlled locations/distances from the electron donor, and (4) an electron acceptor. The rate of electron transfer between the donor and acceptor is modulated by changes in membrane potential and the construct reports on this modulation by a measurable change in donor photoluminescence (PL).

A construct made of the above-listed components (a), (b), and (c) was delivered to the plasma membrane of living cells. The membrane potential was changed by addition of potassium chloride (KCl) and the optical changes in donor PL were recorded. The efficiency of donor PL modulation (quenching) by changes in membrane potential was shown to track with the donor-acceptor separation distance (controlled by peptide design) and the degree of KCl-induced membrane depolarization.

In a first embodiment, a construct for detecting potentials comprises a nanoparticle operable as an electron donor; a modular peptide attached to the nanoparticle, the peptide comprising a nanoparticle association domain, a motif configured to mediate peptide insertion into the plasma membrane, and at least one attachment point for an electron acceptor positioned at a controlled distance from the nanoparticle; and an electron acceptor.

In another embodiment, a method of detecting membrane potential comprises providing a construct according to the first embodiment; contacting a cell with the construct; and detecting emission from the construct, wherein the emission correlates with cellular membrane potential.

In further embodiments, the detecting can be via photoluminescence (PL) and/or photoacoustic (PA) sensing. PA sensing may provide advantages for measurements in tissue—an acoustic signal tends to better traverse a tissue than does a luminescent signal.

BRIEF DESCRIPTION OF THE DRAWINGS

FIGS. 1A-1C show nanoparticle (NP)-based membrane-inserting donor-acceptor electron construct for sensing membrane potential. FIG. 1A is a general scheme of a NP-peptide-electron acceptor assembly. The construct includes (1) a core NP electron donor scaffold with a (2) hydrophilic coating. A modular peptide (3) is self-assembled to the NP surface via a NP-binding domain (4). The peptide further contains a membrane-insertion domain (5) for the insertion of the peptide into the plasma membrane bilayer and has multiple points of attachment for an electron acceptor (6). FIG. 1B is an example schematic in which the NP is a quantum dot (QD), the peptide is a helical-forming peptide that has multiple points for the covalent attachment of a $C_{60}$ fullerene electron acceptor thus allowing control over the donor-acceptor distance and, as a result, the rate of electron transfer from the donor to acceptor. A $His_6$ domain drives assembly of the peptide to the QD surface. FIG. 1C illustrates that at resting potential, the electrons from the photoexcited QD donor are attracted to the positively-charged outer leaflet of the membrane which keeps the QD photoluminescence (PL) on ("QD on"). When the membrane potential reverses (depolarized), electrons from the photoexcited QD are attracted to the positively-charged inner leaflet of membrane and the $C_{60}$ electron acceptor, which quenches the QD PL ("QD off").

FIG. 5A shows DIC (left) and confocal images (right) of cells labeled with QD-JBD1-$C_{60}$ and imaged in an isotonic solution containing 2.5 mM KCl or 140 mM KCl. The samples were excited at 402 nm with a fluorescence detection channels set to 570-

620 nm. (red) with dichroic mirrors at 561 nm. FIG. 5B shows time-resolved quantification of fluorescence emission live HeLa cells labeled with commercial FLUOVOLT, QD-peptide-$C_{60}$ and or QD alone. Image collection began at t=0 when cells were in 100% isotonic solution containing 2.5 mM KCl (0.15 mL). Isotonic solution containing 140 mM KCl was perfused onto the cells at a rate of ~1.0 mL/min (~3 mL total volume added). Fluorescence images were collected every 20 s for 5 min. Fluorescence quantification was done by sampling multiple regions of interest (ROI) in individual cells for each peptide construct. The data represent multiple ROIs from 50-70 cells from 4 independent experiments for each QD-peptide sample.

FIG. 7A shows that PC12 cells tagged with peptide-$C_{60}$ do not produce an appreciable PA signal. However, cells labeled with QD-peptide-$C_{60}$ produces a strong PA signal. FIG. 7B shows that QD-PA signal tracks increase in cell-membrane potential in a monotonic manner. "Wash and repeat" measurements provided in FIG. 7C indicated that QDs could reliably monitor the dynamics of KCl-induced depolarization in a reproducible manner. FIG. 7D shows that the time-course of QD-PA signal in the cell culture (in blue) were consistent with the result from a theoretical model that included diffusion of KCl in the culture dish (in red). Black arrows indicate the time when KCl was administered to the cell-culture dish. Error bars represent standard error of means (n=3).

DETAILED DESCRIPTION

Definitions

Figure 2B:
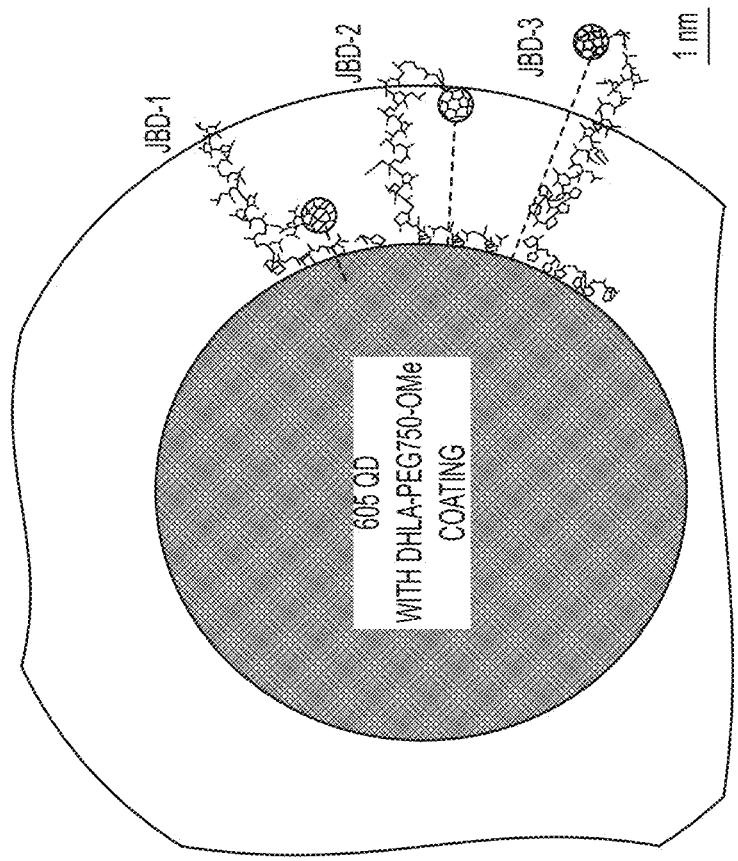
FIGS. 2A and 2B illustrate models of QD-peptide-$C_{60}$ conjugates shows distance dependent positioning of $C_{60}$ and the role of ligand in $C_{60}$ accessibility. Shown is 605 nm-emitting QD capped with (A) DHLA or (B) DHLA-PEG750-OMe ligands. In each case the peptides JBD-1, JBD-2 and JBD-3 are assembled to the QD surface and show the distance-dependent nature of the position of the $C_{60}$ acceptor afforded by the attachment at a unique lysine residue within each peptide sequence. QDs coated with DHLA ligands permit solvent accessibility of the $C_{60}$ moiety when displayed by each of the three peptides while only JBD-3 allows solvent display of the $C_{60}$ on DHLA-PEG750-OMe-capped QDs. Peptide JBD-1 appends the $C_{60}$ closest to the QD center while peptide JBD-3 positions the $C_{60}$ at the most distal position.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

The controlled interfacing of nanoparticle (NP) materials with cellular systems has been employed for a variety of applications including cellular labeling/tracking, imaging, sensing, and drug delivery. NP-biological hybrid bioconjugates (e.g., semiconductor quantum dots (QDs) appended with functional peptides or proteins) are value-added materials wherein the ensemble bioconjugate performs a function not attainable by the individual component materials alone. Such constructs based on energy or charge transfer have much to offer in the development of optical or opto-electrical sensors for assessing cellular states (e.g., health, disease, membrane potential). Sensors aimed at reporting on the electrical activity/membrane potential of cells are critical for understanding the communication process amongst neurons in the brain (brain mapping) as well as for the assessment of the activity of other electrically active cell types (e.g., muscle cells). To date, most opto-electrical sensors for imaging cellular membrane potential are based on either (1) stand-alone electrochromic voltage-sensitive dyes (VSDs) or (2) molecular wires based on electron transfer quenching. VSDs are plagued by poor solubility in aqueous media, nonspecific labeling of non-membrane cellular structures, poor photostability and inherent cytotoxicity. Molecular wires require intricate molecular synthesis and purification strategies, the incorporation of a tailored molecular "wire bridge" to conduct electrons from donor to acceptor, and often use poorly photostable molecular fluorophores (e.g., fluorescein) as the optical readout moiety. Cumulatively, these issues represent significant limitations of currently available electro-optical materials for optically sensing membrane potential.

Described herein is a bioconjugate including a modular, multifunctional nanoparticle-based electron donor-acceptor bioconjugate for the realtime perception of changes in cellular membrane potential. The construct comprises the following components: (a) a photoluminescent NP electron donor, (b) a modular, multidomain membrane insertion peptide, and (c) an electron acceptor (FIG. 1A). The peptide includes (1) a NP association domain, (2) amino acid motifs to mediate peptide insertion into the plasma membrane, (3) one or more attachment points for attachment of an electron acceptor at discreetly controlled locations/distances from the electron donor, and (4) an electron acceptor. The rate of electron transfer between the donor and acceptor is modulated by changes in membrane potential and the construct reports on this modulation by a measurable change in donor photoluminescence (PL). FIG. 1B shows a specific example of the donor-acceptor bioconjugate where the electron donor is a semiconductor quantum dot (QD) that is connected to an electron acceptor, a carbon allotrope ($C_{60}$ or fullerene) via a membrane-insertion peptide. FIG. 1C shows a schematic representation of the QD-peptide-$C_{60}$ construct reporting on the transition of the cell from resting potential state (QD signal "on") to depolarized state (QD signal "off").

Examples

Peptides of varying lengths and attachment points for the $C_{60}$ fullerene electron acceptor were synthesized and iteratively tested for their ability to quench the excited state QD donor (Table 1). These peptides each contain a $His_6$ tract to mediate attachment of the peptide to the ZnS shell of the QD. Each peptide also bears a unique lysine residue for the covalent attachment of the $C_{60}$ to position the $C_{60}$ moiety at discreetly controlled distances from the QD donor center. The peptides in Table 1 have sequence identification as follows: JBD-1 is SEQ ID No: 1; JBD-2 is SEQ ID No: 2; and JBD-3 is SEQ ID No: 3.

TABLE 1

Multifunctional modular peptides for membrane insertion and QD-coupled membrane potential sensing.

| Peptide | Sequence* |
|---------|-----------|
| JBD-1 | Ac-AAAALAAAAALAALAA<u>K</u>AAAGGH$_6$-COOH |
| JBD-2 | Ac-<u>K</u>AAALAAAAALAAWAALAAAGGH$_6$-COOH |
| JBD-3 | Ac-<u>K</u>AAALAAAAALAAWAALAAAP$_9$GGH$_6$-COOH |

*N terminus blocked with an acetyl group; C terminus blocked with an amide
<u>K</u> = unique lysine for attachment of C$_{60}$ electron acceptor Peptides of varying lengths and attachment points for the C$_{60}$ fullerene electron acceptor were synthesized and iteratively tested for their ability to quench the excited state QD donor (Table 1). These peptides each contain a His$_6$ tract to mediate attachment of the peptide to the ZnS shell of the QD. Each peptide also bears a unique lysine residue for the covalent attachment of the C$_{60}$ to position the C$_{60}$ moiety at discreetly controlled distances from the QD donor center.

Figure 2A:
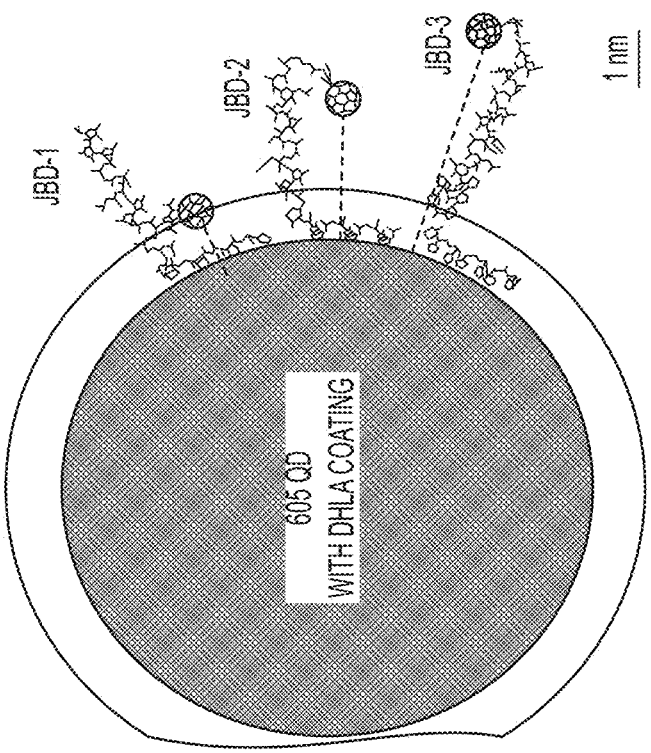
Figure 3A:
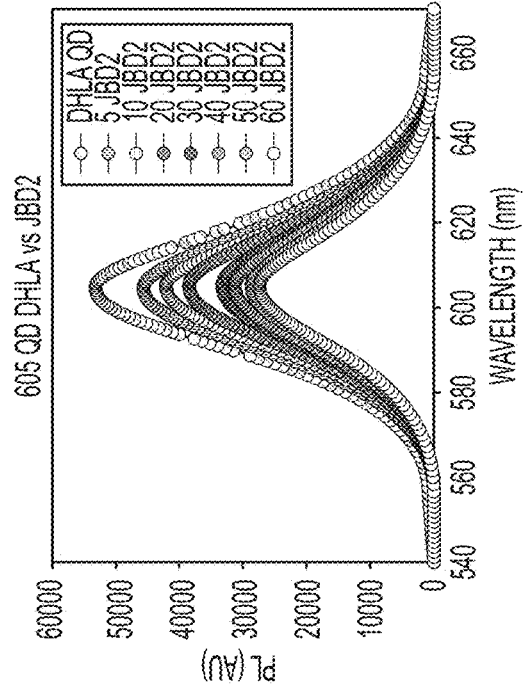
FIGS. 3A-3D show steady state quenching of QD PL by peptide-$C_{60}$ is dependent on peptide ratio and QD-$C_{60}$ separation distance. Each peptide was assembled onto a fixed amount of QD at the ratios shown and spectra collected. Shown are the quenching spectra for $C_{60}$ peptide conjugates of (A) JBD-1, (B) JBD-2 and (C) JBD-3 on DHLA-capped QDs. The quenching efficiency for each peptide as a function of peptide ratio (valence) is shown in FIG. 3D. The data show the valence- and $C_{60}$ distance-dependent nature of the efficiency of peptide-$C_{60}$-mediated QD quenching.
Figure 3B:
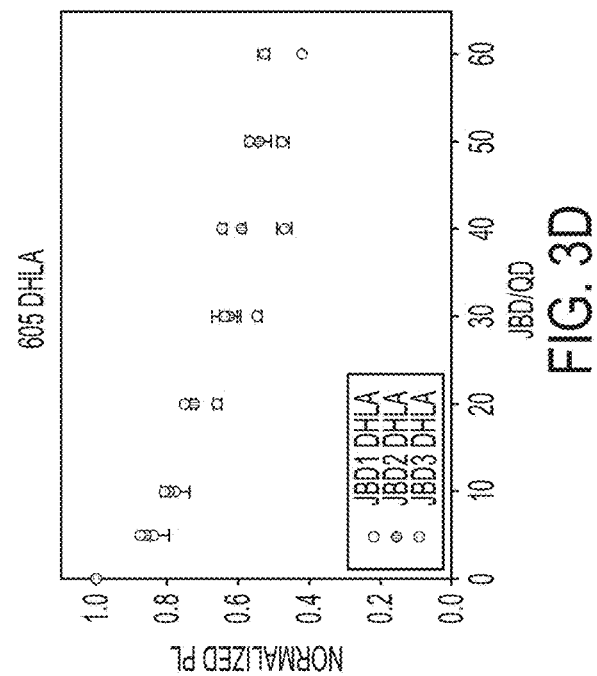
Figure 3C:
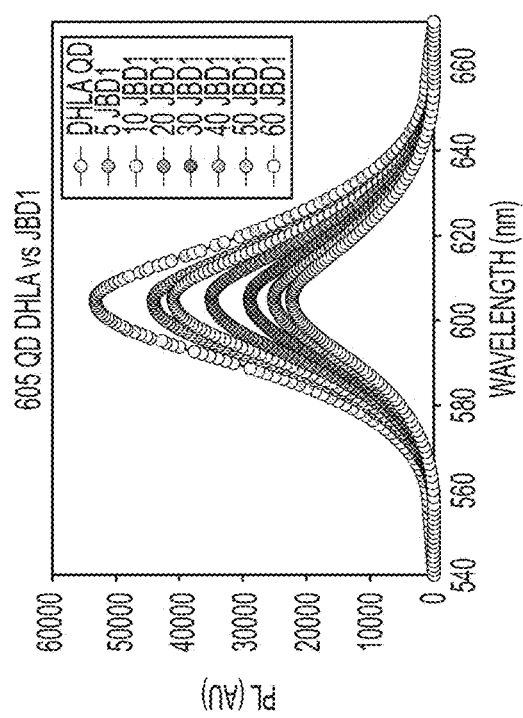
Figure 3D:
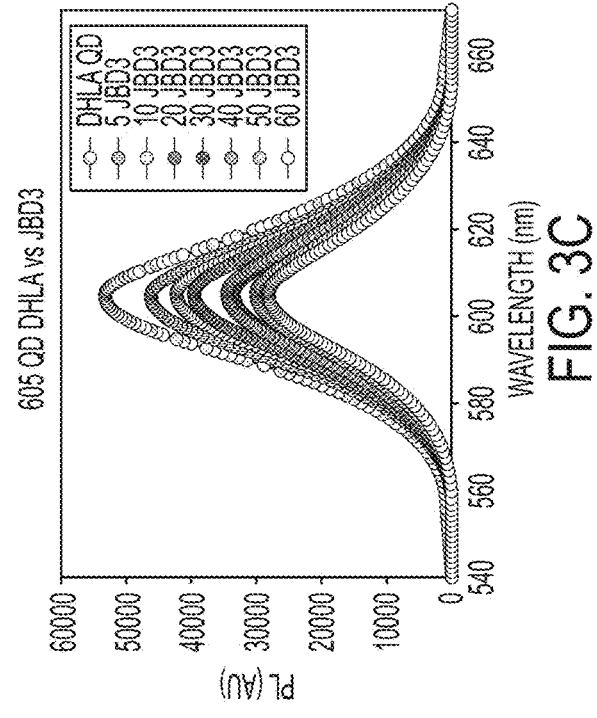

Molecular modeling of the orientation of the three peptide species once assembled to the QD via the His$_6$ tract revealed the predicted orientation and distance of the C$_{60}$ acceptor from the QD center when presented to the QD as a covalently attached moiety to the peptide backbone. In the progression from peptide JBD-1 to JBD-3, the C$_{60}$ acceptor is positioned at increasingly further distances from the QD center (FIG. 2). It is clear from the modeling that the nature of the hydrophilic ligand on the QD surface impacts the solvent accessibility of the C$_{60}$ moiety. QDs coated with dihydrolipoic acid (DHLA) ligands showed complete display of the C60 by peptides JBD-2 and JBD-3 and partial display in the context of peptide JBD-1. QDs coated with DHLA-PEG750-OMe (pegylated DHLA capped with a terminal methoxy group) showed display of the C$_{60}$ only in the context of peptide JBD-3 while in the other two peptide species the C$_{60}$ was buried within the ligand layer. As the DHLA-coated QDs mediated better cell binding than DHLA-PEG750-OMe, DHLA QD-peptide-C$_{60}$ complexes were used for cellular assays.

Steady state fluorescence measurements were performed to determine the efficiency of electron transfer between the QD and the various peptide-C$_{60}$ species. The readout for the assay is the quenching of QD PL upon attachment of the peptide-C$_{60}$ conjugate to the QD surface. Two key parameters were assessed for their role in affecting efficient quenching of the photo-excited QD donor: (1) peptide-C$_{60}$ valence (or number of peptide-C$_{60}$ conjugates arrayed around the QD surface) and (2) the distance of the C$_{60}$ electron acceptor from the QD donor center. As shown in FIG. 3 each peptide-C$_H$ species displayed the ability to efficiently quench the PL emission of the QD donor in a ratiometric manner (i.e., the quenching efficiency increased as the number of peptides arrayed around the QD increased).

Figure 4:
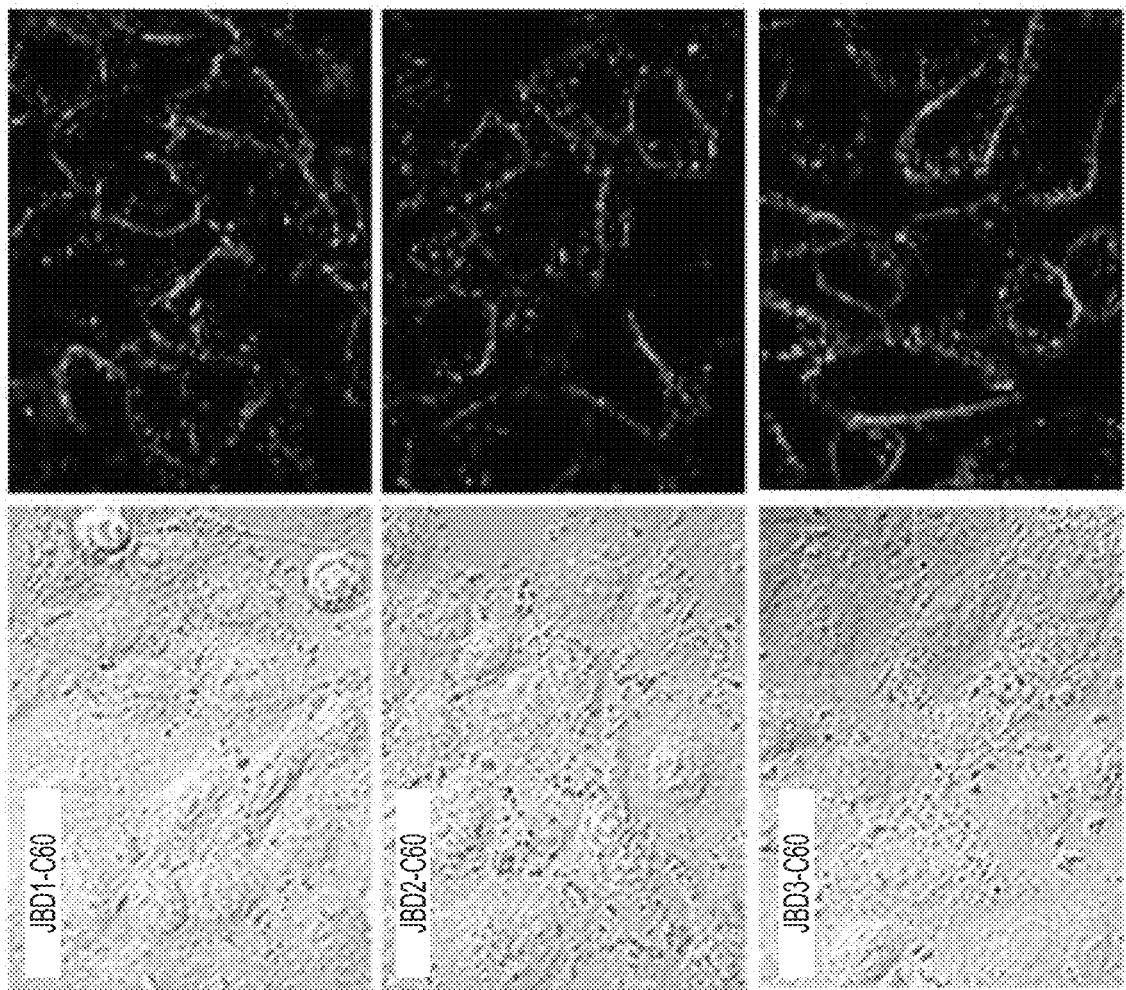
FIG. 4 shows confocal laser scanning microscopy (CLSM) images of A549 cells stained with QD-peptide-$C_{60}$ complexes. Shown are differential interference contrast (DIC) (left) and confocal microscopy images (right) showing fluorescence emission of QD-peptide-$C_{60}$ bound to A549 cells. The cells were incubated with 20 nM QD complexed with JBD-1-C60 peptides (QD:peptide ratio 1:20) in PBS (pH 8.2) for 10 min at 37° C. For imaging the samples were excited at QD excitation at 402 nm with fluorescence detection channel set to 570-620 nm (red). A dichroic mirror at 561 nm was used to reflect incident excitation light.

Next, fluorescence imaging was used to confirm the successful labeling of the plasma membrane with the QD-peptide-C$_{60}$ conjugates. A549 (human lung adenocarcinoma) cells were labeled with 605 QD-DHLA-peptide-C$_{60}$ conjugates and compared to cells incubated with QD alone. FIG. 4 shows DIC and corresponding fluorescence micrographs of A549 cells labeled with the various QD-peptide-C$_{60}$ constructs. The cellular labeling is clearly membranous, consistent with the insertion of the peptide-C$_{60}$ moiety into the plasma membrane and the docking of the QD onto the surface of the plasma membrane. Immuno-silver staining assays confirmed the insertion of the C$_{60}$ moiety into the aliphatic portion of the plasma membrane.

Figure 5A:
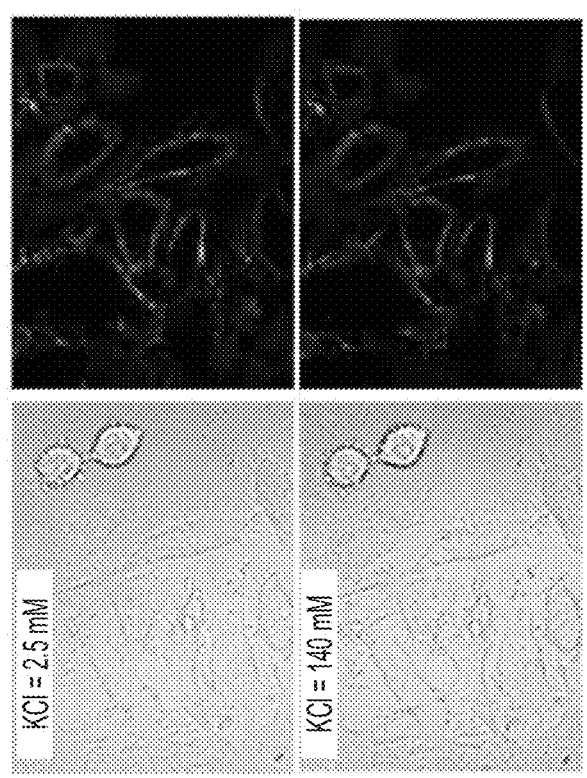
FIGS. 5A and 5B are confocal images and time-resolved quantification of fluorescence emission of live HeLa cells in resting and depolarizing state using different potassium chloride (KCl) solutions, respectively.

The ability of the QD-peptide-C$_{60}$ systems to visualize changes in membrane potential was confirmed by performing depolarization experiments on HeLa (human cervical carcinoma) cells that were labeled with the QD-peptide-C$_{60}$ conjugates. The cells were depolarized with an isotonic solution containing 140 mM potassium chloride (KCl). Incubation of cells in this solution causes depolarization of the cells by the influx of K$^+$ ions through K$^+$ leak channels. FIG. 5A shows representative confocal fluorescence images for cells labeled with QD-JBD-1-C$_{60}$ conjugates before and after the addition of the KCl solution.

Figure 5B:
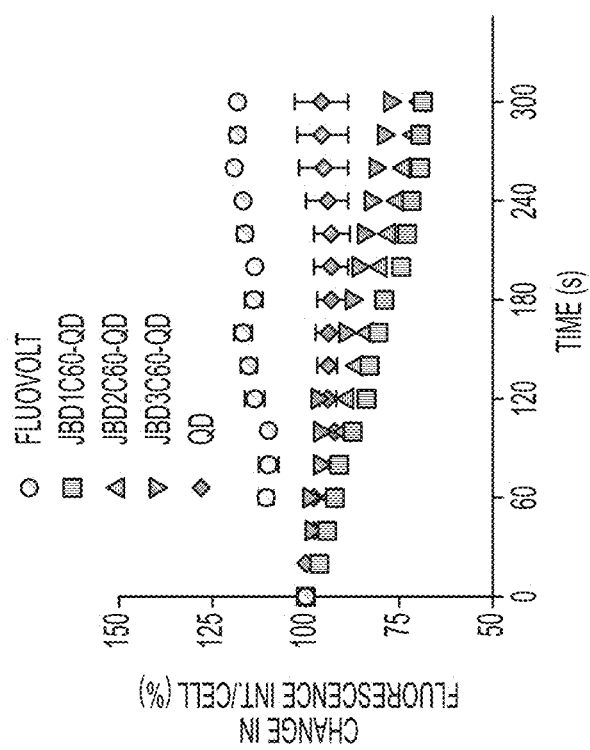

The images clearly show the time-resolved reduction in QD PL upon perfusion of the KCl solution onto the cells and subsequent depolarization. Similar responses for QD-peptide conjugates of JBD-2-C$_{60}$ and JBD-3-C$_{60}$ were obtained (images not shown). A graph of the resulting time-resolved PL intensities in response to depolarization is shown in FIG. 5B. Minimal change in PL of QDs not decorated with the peptide-C$_{60}$ conjugates was noted, clearly demonstrating the dependence of the response on the presence of the peptide-C$_{60}$ conjugate. Also included is a comparison of QD-peptide-C$_{60}$-derived cellular response to that obtained in HeLa cells labeled with a "state-of-the-art" molecular wire-based membrane potential probe (FLUOVOLT; commercially available from ThermoFisher). For comparison, the QD-JBD-1-C$_{60}$ conjugate exhibited a maximum response (PL decrease) of 31% at 5 min while the FLUOVOLT probe displayed a fluorescence response of 19% (PL increase) over this same time course. These data clearly demonstrate the superior sensitivity of the QD-JBD-1-C$_{60}$ conjugate compared to the commercial probe. Further, the magnitude of the QD PL response exhibited a distinct distance dependent response to depolarization. The PL response tracked inversely with the separation distance between the QD donor center and the C$_{60}$ moiety, in good agreement with the plate-based steady state data presented in FIG. 3.

Figure 6B:
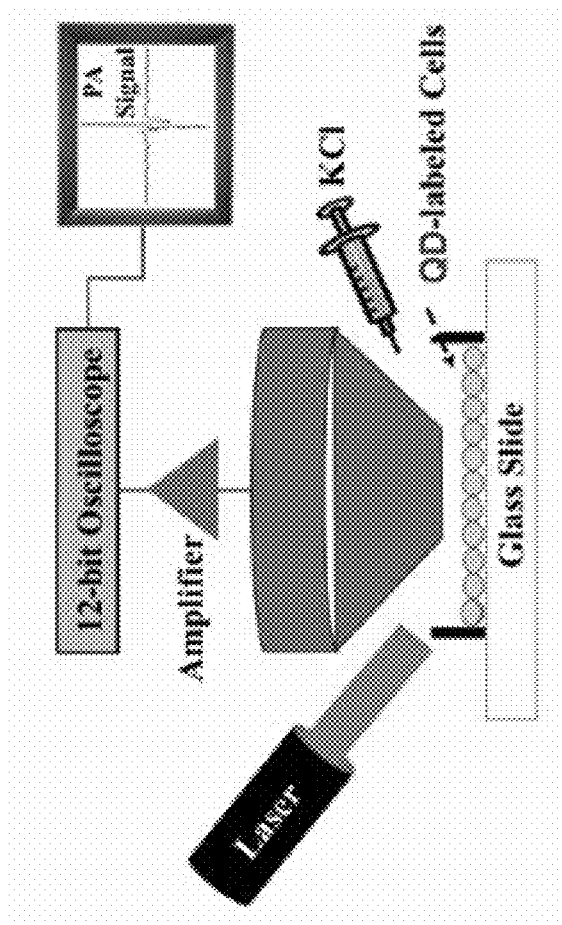
FIGS. 6A and 6B schematically illustrate an exemplary patch-clamp setup for calibrating the QD-PL signal with respect to the cell membrane potential and an exemplary setup for characterizing the PA response from QD-tagged cells while chemically inducing cell depolarization, respectively.
Figure 6A:
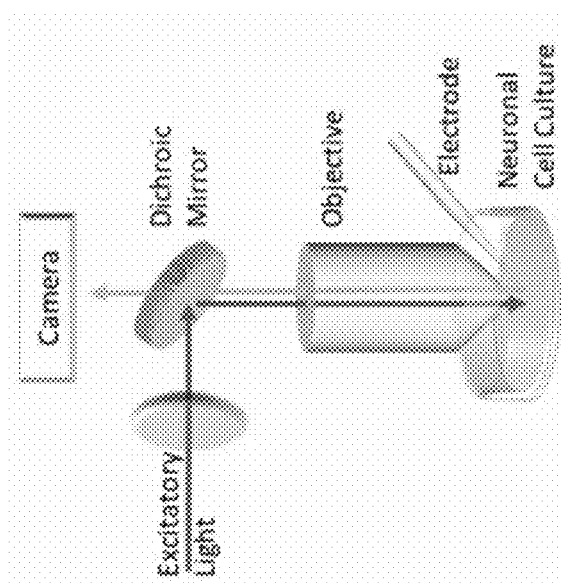

The PL response of the QD-bioconjugates was cross-validated and calibrated using a whole-cell patch clamp operating in the current-clamp mode in as depicted in FIG. 6A. The patch-clamp was used to incrementally, step-wise increase the cell membrane potential of a QD-tagged PC12 cell from resting potential while a high-sensitivity video microscope measured the QD-PL response from a that cell for each voltage step. The QD-PL signal exhibited a fractional change of ~0.05 (5%) when the cell membrane potential was increased from resting voltage of ~70 mV to 10 mV (data not shown). Therefore, the corresponding QD-PL sensitivity was determined to be 0.06% per mV, which compares well to other commercially available voltage-sensitive fluorescence dyes. Two-way ANOVA analysis indicated that the mean fractional change in QD-PL for increasing cell membrane potential was indeed statistically different from that at resting potential (p=0.0003).

Photoacoustic Sensing

In addition to the photoluminescent embodiments, sensing can be accomplished using a photoacoustic (PA) technique with the same types of constructs as used in the previous examples with PL. The constructs include an electron donor such as a quantum dot associated with a modular peptide, and an electron acceptor. In an exemplary embodiment, a CdSe—CdS/ZnS core-shell quantum dot of 8.4 nm diameter acts as the electron donor and $C_{60}$ is the electron acceptor.

PA sensing relies on absorption of light and subsequent thermoelastic generation of ultrasound. Various PA-based methods can provide spectroscopic specificity to endogenous and exogenous chromophores, but the molecular information is relayed to the sensor acoustically, which is not as susceptible to scattering in tissue as light. Therefore, PA potentially can provide a reasonable compromise between spatial resolution (dependent on the focusing properties of the ultrasound receiver) and imaging depth (superior to fluorescence). PA-based techniques are potentially well suited for studying brain function in small-animal models.

In PA sensing, the illuminated QD dissipates heat locally into the cell membrane. This heat can be detected as generated pressure/sound waves, for example by using an acoustic microphone or transducer. In embodiments, a PA emission is detected using an ultrasound transducer, optionally amplified, and the resulting signal transmitted for recording and analysis, for example to an oscilloscope and/or digitizer.

An exemplary arrangement for PA sensing is illustrated in FIG. 6B. The temporal change in the QD-PA signal during KCl-induced cell depolarization was observed. A 532-nm laser with a pulse duration of 5 ns and a pulse-repetition frequency of 10 Hz was used for exciting the QD-probes with an incident fluence of 5 mJ/cm$^2$. A focused ultrasound transducer with 20-MHz bandwidth (FWHM beam width of 0.5 mm) detected the PA signals produced by QD-tagged cells in a culture dish. QD-PA signals were amplified using a 20-dB low-noise amplifier and recorded using a 12-bit digitizer.

QD-PA signals were recorded in separate experiments (each n=3) for depolarization achieved using four concentrations of KCl: 2.5, 8, 17, and 29 mM. A previously developed theoretical model (verified using a patch clamp), was used to determine the corresponding increase in cell-membrane potential. The change in cell-membrane potential corresponding to the concentrations used were estimated to be 10, 20, 30, and 40 mV respectively. In order to confirm that addition of KCl did not produce deleterious effects on the cells, and to demonstrate the ability of QD probes to track changes in membrane potential in a reproducible manner, "wash and repeat" experiments were performed on a cell culture using 17 mM KCl (30 mV increase in membrane potential). Lastly, QD-PA experiments were also performed using a KCl concentration of 10 mM to facilitate a head-to-head comparison with QD-PL based monitoring of KCl-induced depolarization.

Figure 7B:
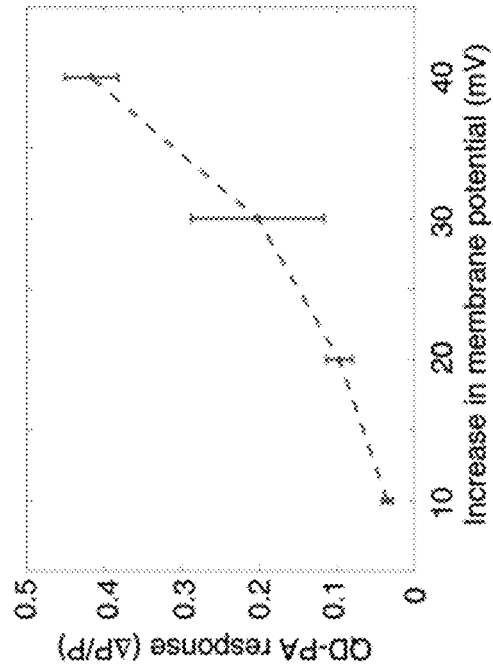
FIGS. 7A-7D illustrate measurements of QD-PA signal.
Figure 7A:
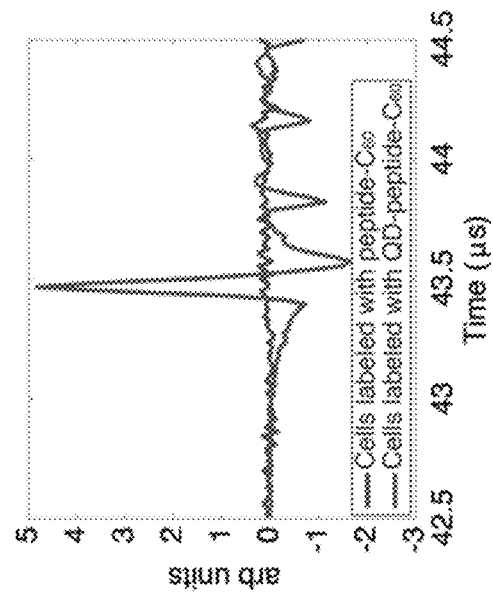

FIG. 7A shows the photoacoustic response from PC12 cells tagged with the complete QD-based voltage-sensing construct (QD-JBD1peptide-$C_{60}$) as well as cells tagged with just the peptide-$C_{60}$ conjugates. As shown, in the absence of the QD, there is negligible PA response, indicating the critical role of the QD in mediating the generation of the PA signal.

Figure 7D:
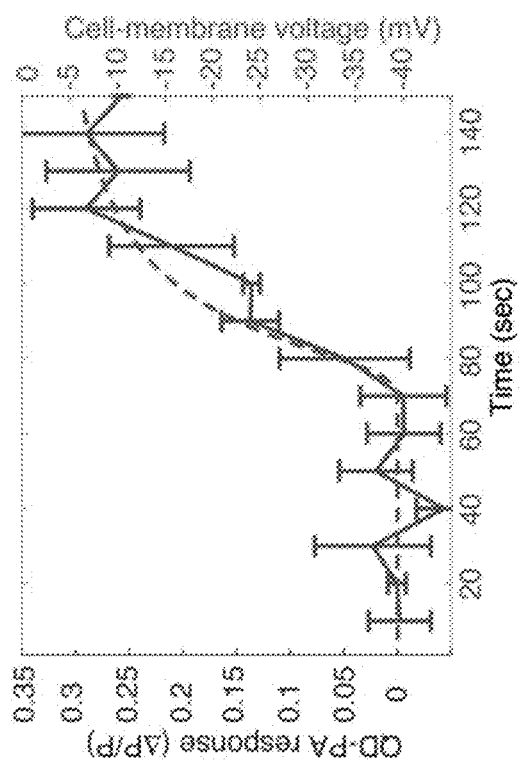
Figure 7C:
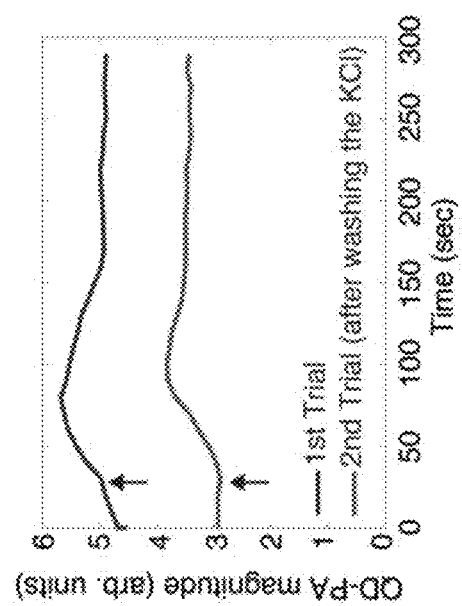

The amplitude of the QD-PA signal monotonically tracked an increase in membrane potential of the cell culture (FIG. 7B). The amplitude of the QD-PA signal (average of ten waveforms) was monitored over time while the PC12 cells were depolarized by adding KCl (17 mM). The QD-PA signal tracked exhibited dynamics associated with KCl-induced depolarization. When excess KCl was washed, QD labeling of cells decreased resulting a ~30% reduction in the baseline QD-PA signal. However, when KCl was re-administered, the QD-PA signal reproducibly tracked the depolarization dynamics (FIG. 7C). The time-course of depolarization observed from the QD-PA signals was consistent with the results of the theoretical model that accounted for KCl diffusion in the culture dish (FIG. 7D).

Figure 8:
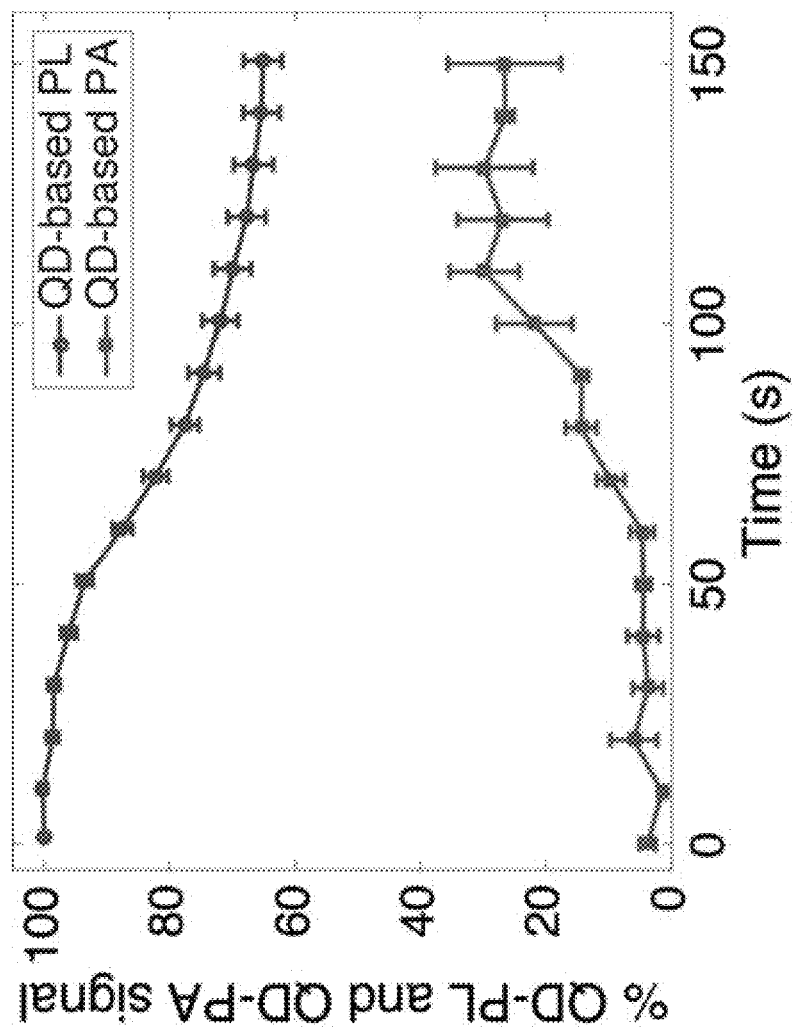
FIG. 8 shows that the change in the QD-PA signal from cells depolarized by adding KCl exhibits dynamics that were similar to those tracked using the QD-PL signal. Mean QD-PA and QD-PL values were obtained from (n=3) cell cultures and the error bars represent standard error of means.

It is also possible to measure cell depolarization using both PL and PA modes. FIG. 8 shows the QD-PL and QD-PA signals when 10 mM of KCl was administered to the cell cultures: both measures exhibited a similar dynamic change. QD-PL and QD-PA exhibited over 20% change in signal due to KCl-induced depolarization. Furthermore, QD-PA signal tracked the time profile of the QD-PL signal in the time course of 150 seconds.

Concluding Remarks

Potential application areas include those where stable, long term imaging of changes in membrane potential are desired, for example imaging/optical recording of the electrical activity in one or more cultured cells, or in tissue slices, whole issues, and/or animals. Targeted cell types in these applications would include (but are not limited to) electrically active cells such as neurons and muscles cells. These material constructs could also find utility in quantum dot-based LED cells where the tuning of QD luminescence in the presence of an electric field is desired/required.

Advantages of NP-peptide-acceptor assemblies as described herein include the following. They are potentially amenable to both covalent and noncovalent attachment strategies. Modular design of functional domains allows for flexibility in iterative peptide development and testing. The strategy is amenable to the assembly of conceivably any class of NP with any modular, multifunctional polymer. The NP surface can be functionalized with different types of modular, multifunctional peptides ("mixed" surfaces) giving ratiometric control over the nature of the decorated NP surface and iterative control over the rate of donor-acceptor electron transfer.

More particular advantages of the QD-peptide-$C_{60}$ construct described herein include the following. The peptide self-assembles noncovalently to the QD donor surface without the need for complex covalent attachment chemistries that use high concentrations of excess reactants that require purification. The peptide assembles to the QD rapidly (10 min) with high (nM) affinity. The assembled construct labels cell membranes rapidly (10 minutes) after conjugate assembly, with 20 minutes total time for cellular labeling with the QD-peptide constructs. The peptide linker does not conduct, shuttle or otherwise direct the transfer of electrons from the donor to the acceptor which simplifies the design and synthesis of QD-C60 linkers. Electron transfer is completely distance-dependent which is a key distinguishing factor relative to other membrane potential imaging molecular wires (e.g., FLUOVOLT sold by ThermoFisher), and this dependency can be iteratively controlled by controlling the donor-acceptor separation distance. Furthermore, the ratio or valence (and thus the avidity) of the peptide for the NP can be controlled and can be used to tune the rate or efficiency of donor quenching/electron transfer. The exceptional photostability of QD-based constructs allows for much longer imaging times (>100×) compared to voltage-sensitive dyes. The significantly large two-photon action cross section of QD materials ($10^2$-$10^3$ greater than organic dyes) makes them ideal for deep tissue imaging.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

All documents mentioned herein are hereby incorporated by reference for the purpose of disclosing and describing the particular materials and methodologies for which the document was cited.

REFERENCES

Assembly of Peptides onto the Surface of QDs and QD-Based Charge Transfer

Stewart, M. H., et al., *Competition between Förster resonance energy transfer and electron transfer in stoichiometrically assembled semiconductor quantum dot fullerene conjugates*. ACS Nano, 2013. 7(10): 9489-9505.

Medintz, I. L. et al., *Quantum-dot/dopamine bioconjugates function as redox coupled assemblies for in vitro and intracellular pH sensing*. Nat. Mater. 2010. 9: 676-684.

Mao, C., et al., *Viral assembly of oriented quantum dot nanowires*. Proc Natl Acad Sci USA, 2003. 100(12): p. 6946-51.

Medintz, I. L., et al., *A reactive peptidic linker for self-assembling hybrid quantum dot-DNA bioconjugates*. Nano Lett, 2007. 7(6): p. 1741-8.

Medintz, I. L., et al., *Intracellular Delivery of Quantum Dot-Protein Cargos Mediated by Cell Penetrating Peptides*. Bioconjug Chem, 2008.

Slocik, J. M., et al., *Peptide-assembled optically responsive nanoparticle complexes*. Nano Lett, 2007. 7(4): p. 1054-8.

Soman, C. P. and T. D. Giorgio, *Quantum dot self-assembly for protein detection with sub-picomolar sensitivity*. Langmuir, 2008. 24(8): p. 4399-404.

Susumu, K, et al., *Enhancing the stability and biological functionalities of quantum dots via compact multifunctional ligands*. J Am Chem Soc. 2007 129(45):p 13987-96.

Sapsford K, et al., *Kinetics of metal-affinity driven self-assembly between proteins or peptides and CdSe-ZnS quantum dots*. J. Physical Chem. C. 2007. 111:p. 11528-11538.

Cellular Uptake of and Membrane Labeling with QD-Peptide Assemblies

Delehanty, J. B. et al. *Delivering quantum-dot peptide bioconjugates to the cellular cytosol: escapingfrom the endolysosomal system*. Integrat. Biol. 2010. 2:265-277.

Boeneman, K., et al., *Selecting improved peptidyl motifs for cytosolic delivery of disparate protein and nanoparticle materials*. ACS Nano. 2013. 7(5): 3778-3796.

Rozenzhak, S. M., et al., *Cellular internalization and targeting of semiconductor quantum dots*. Chemical Communications, 2005(17): p. 2217-2219.

Derfus, A. M., W. C. W. Chan, and S. N. Bhatia, *Intracellular delivery of quantum dots for live cell labeling and organelle tracking*. Advanced Materials, 2004. 16(12): p. 961-+.

Lagerholm, B. C., et al., *Multicolor coding of cells with cationic peptide coated quantum dots*. Nano Letters, 2004. 4(10): p. 2019-2022.

Ruan, G., et al., *Imaging and tracking of tat peptide-conjugated quantum dots in living cells: new insights into nanopartide uptake, intracellular transport, and vesicle shedding*. J Am Chem Soc, 2007. 129(47): p. 14759-66.

Lei, Y., et al., *Applications of mesenchymal stem cells labeled with Tat peptide conjugated quantum dots to cell tracking in mouse body*. Bioconjug Chem, 2008. 19(2): p. 421-7.

Chang, J. C., H. L. Su, and S. H. Hsu, *The use of peptide-delivery to protect human adipose-derived adult stem cells from damage caused by the internalization of quantum dots*. Biomaterials, 2008. 29(7): p. 925-36.

Lieleg, O., et al., *Specific integrin labeling in living cells using functionalized nanocrystals*. Small, 2007. 3(9): p. 1560-5.

Shah, B. S., et al., *Labeling of mesenchymal stem cells by bioconjugated quantum dots*. Nano Lett, 2007. 7(10): p. 3071-9.

Biju, V., et al., *Quantum dot-insect neuropeptide conjugates for fluorescence imaging transfection, and nucleus targeting of living cells*. Langmuir, 2007. 23(20): p. 10254-61.

Lieleg, O., et al., *Specific integrin Labeling in living Celts using functionalized nanocrystals*. Small, 2007. 3(9): p. 1560-1565.

Medintz, I. L., et al., *Intracellular Delivery of Quantum Dot-Protein Cargos Mediated by Cell Penetrating Peptides*. Bioconjug Chem, 2008. 19: 1785:1795.

Membrane-Inserting Peptides

Boeneman, K., et al., *Selecting improved peptidyl motifs for cytosolic delivery of disparate protein and nanoparticle materials*. ACS Nano. 2013. 7(5): 3778-3796.

Optical molecular wires for visualizing changes in membrane potential

Woodford, C. R., et al. *Improved PeT molecules for optically sensing voltage in neurons*. J. Am. Chem. Soc. 2015. 137: 1817-1824.

Huang, Y-L., et al. *A photostable silicon rhodamine platform for optical voltage sensing*. J. Am. Chem. Soc. 2015. 137: 10767-10776.

Davis et. al. Molecular-wire behavior in p-phenylenevinylene oligomers. Nature 1998. 396: 60-63.

Photo Acoustic Sensing

S. Chemla and F. Chavane, "Voltage-sensitive dye imaging: Technique review and models," Journal of Physiology-Paris 104, 40-50 (2010).

A. Grinvald and R. Hildesheim, "VSDI: a new era in functional imaging of cortical dynamics," Nature Reviews Neuroscience 5, 874-885 (2004).

N. Vogt, "Voltage sensors: challenging, but with potential," Nature Methods 12, 921-924 (2015).

N. Dana, R. A. Fowler, A. Allen, J. Zoldan, L. Suggs, and S. Emelianov, "In vitro photoacoustic sensing of calcium dynamics with arsenazo III," Laser Physics Letters 13, 075603 (2016).

D. Wang, Y. Wu, and J. Xia, "Review on photoacoustic imaging of the brain using nanoprobes," Neurophotonics 3, 010901 (2016).

J. Yao and L. V. Wang, "Photoacoustic brain imaging: from microscopic to macroscopic scales," Neurophotonics 1, 011003-011003 (2014).

S. Hu and L. V. Wang, "Neurovascular Photoacoustic Tomography," Frontiers in Neuroenergetics 2(2010).

What is claimed is:

1. A method of detecting cellular membrane potential, the method comprising:
providing a construct comprising a quantum dot operable as an electron donor; a modular peptide attached to the quantum dot, the peptide comprising a nanoparticle association domain, a motif configured to mediate peptide insertion into a cellular plasma membrane, and at least one attachment point for an electron acceptor positioned at a controlled distance from the quantum dot; and an electron acceptor comprising $C_{60}$;
contacting a cell with the construct; and
detecting a photoacoustic emission from the construct, wherein the photoacoustic emission correlates with cellular membrane potential,
wherein the modular peptide is selected from the group consisting of SEQ ID NO: 1, SEQ ID NO: 2, and SEQ ID NO: 3; and
wherein the photoacoustic emission occurs in the absence of aggregation of the construct.

2. The method of claim 1, wherein the cell is in a tissue.

3. The method of claim 2, wherein the tissue is in a living animal.

* * * * *